United States Patent
Verhoeyen et al.

(10) Patent No.: US 7,833,962 B2
(45) Date of Patent: Nov. 16, 2010

(54) METHOD OF REDUCING HYPERTENSION BY ADMINISTERING FLAVANOL GYLCOSIDES

(75) Inventors: Martine Elisa Verhoeyen, Sharnbrook (GB); Sheila Ann Wiseman, Vlaardingen (NL)

(73) Assignee: Conopco, Inc., Englewood Cliffs, NJ (US)

( * ) Notice: Subject to any disclaimer, the term of this patent is extended or adjusted under 35 U.S.C. 154(b) by 592 days.

(21) Appl. No.: 10/566,806

(22) PCT Filed: Jun. 18, 2004

(86) PCT No.: PCT/EP2004/006598

§ 371 (c)(1),
(2), (4) Date: Dec. 17, 2007

(87) PCT Pub. No.: WO2005/013722

PCT Pub. Date: Feb. 17, 2005

(65) Prior Publication Data

US 2008/0107792 A1 May 8, 2008

(30) Foreign Application Priority Data

Jul. 31, 2003 (GB) ................................. 0317985.0

(51) Int. Cl.
*A01N 61/00* (2006.01)
(52) U.S. Cl. .......................................................... 514/1
(58) Field of Classification Search ...................... None
See application file for complete search history.

(56) References Cited

U.S. PATENT DOCUMENTS

2003/0101477 A1  5/2003 Colliver et al.

FOREIGN PATENT DOCUMENTS

| EP | 1 254 960 | * 11/2002 |
|---|---|---|
| JP | 3004769 | 1/1991 |
| JP | 2000116363 | 4/2000 |
| JP | 2001240539 | 9/2001 |
| JP | 2002171934 | 6/2002 |
| WO | 99/37794 | 7/1999 |
| WO | WO 99/37794 | * 7/1999 |
| WO | 00/04175 | 1/2000 |
| WO | WO 00/04175 | * 1/2000 |
| WO | 2002/20030 A2 | 3/2002 |

OTHER PUBLICATIONS

Duarte et al, British Journal of Pharmacology, vol. 133, p. 117-124, 2001.*
Bovy, et al., "High-Flavonol tomatoes resulting from the heterologous expression of the maize transcription factor genes LC and CI", plant cell, vol. 14, No. 10, Oct. 2002, pp. 2509-2526, XP002295919.
Verhoeyen, et al., "Increasing antioxidant levels in tomatoes through modification of the flavonoid biosynthetic pathway", J. Exp Botany (2002), 377:2099-2106.
Duarte, et al., "Antihypertensive effects of the flavonoid quercetin in spontaneously hypertensive rats", British Journal of Pharmacology, 2001 United Kingdom, vol. 133, No. 1, 2001, pp. 117-124, XP002295921.
Muir, et al., "Overexpression of petunia chalcone isomerase in tomato results in fruit containing increased levels of flavonols", Nature Biotechnology, vol. 19, No. 5, May 2001, pp. 470-474. XP002295920.
Matsubara, et al., "Structure and hypotensive effect of fiavonoid glycosides in citrus unshiu peelings", XP002295923, abstract, and Agricultural & Biological Chemistry, vol. 49, No. 4, 1985, p. 909.
GB Search Report GB 0317985.0 dated Nov. 25, 2003.

* cited by examiner

*Primary Examiner*—Eileen B O Hara
(74) *Attorney, Agent, or Firm*—Michael P. Aronson

(57) ABSTRACT

The present invention relates to use of a plant which has been modified to produce increased levels of flavonol glucosides, or an extract thereof containing flavonol glucosides, in reducing hypertension in a mammal.

8 Claims, 6 Drawing Sheets

A

B

A

B

A

B

A

B

A

B

A

B

METHOD OF REDUCING HYPERTENSION BY ADMINISTERING FLAVANOL GYLCOSIDES

FIELD OF THE INVENTION

Figure 1:
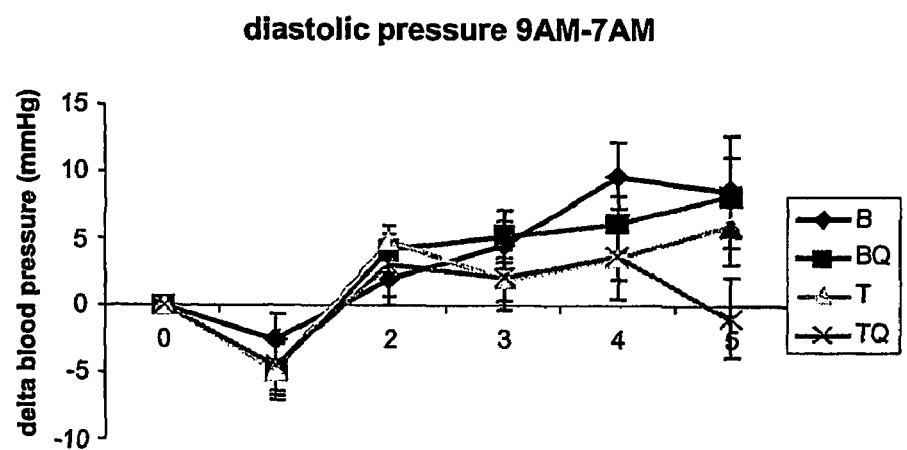
Figure 1:
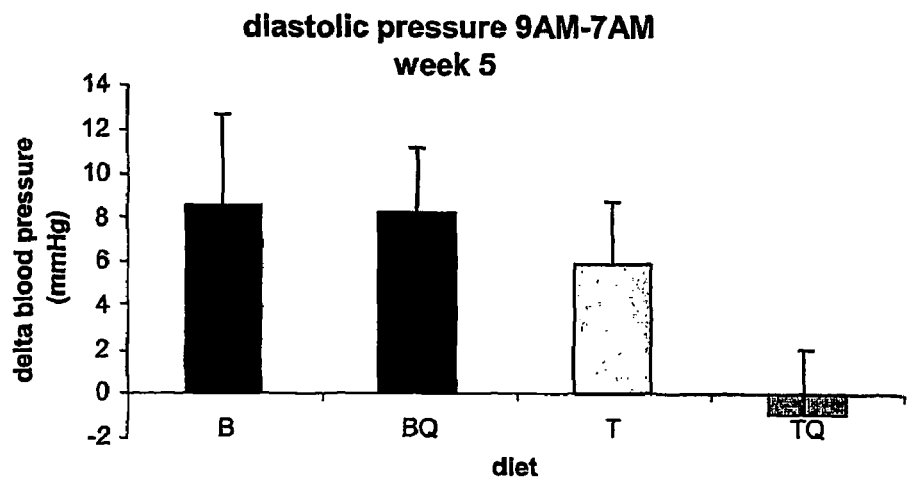

The present invention relates to use of a plant or plant extract, preferably a vegetable or fruit, which exhibits increased levels of flavonol glucosides in the reduction of hypertension in mammals, such as man, and novel products containing those flavonol glucosides.

BACKGROUND OF THE INVENTION

Flavonoids are polyphenolic compounds that occur ubiquitously in foods of plant origin and are well known for their antioxidant capacities. Major dietary sources of flavonoids are vegetables, fruits, and beverages such as tea and red wine. Among the dietary flavonoids, quercetin-glycosides are amongst the most abundant. Flavonoids in general have been reported to confer a number of health benefits and are believed to act by intervention in various metabolic pathways such as by inhibition of 5-cyclooxygenase. Included within the general term flavonoid are flavonols, flavones, flavanones, catechins, anthocyanins, isoflavonoids, dihydroflavonols and stilbenes.

The main types of flavonols found in plants are based on quercetin, kaempferol and myrecetin, and their respective glycosides.

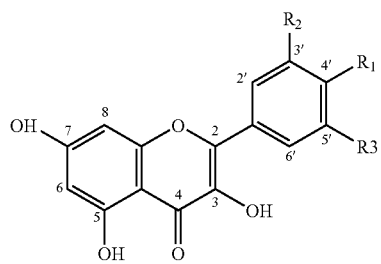

Kaempferol: R1 = OH, R2 = H, R3 = H
Quercetin:  R1 = OH, R2 = OH, R3 = H
Myrecetin:  R1 = OH, R2 = OH, R3 = OH This figure depicts the three different flavonol aglycones (no sugars attached). The sugars are usually attached to the 3 and 7 positions, but attachments on the 4' and 3' and possibly even 5 positions feature as well. The sugars are either attached as monomers, dimers and sometimes trimers. Sugars include glucose, rhamnose, galactose, xylose and arabinose. More than one attachment site can be used, although 4 sugars appears to be the maximum number observed. Flavonols represent a large class of molecules all based on a small number of core structures and natural variation is achieved by attachment of other molecular entities e.g. sugar, methyl groups etc, at different positions of the flavonol core-ring structure. Glycosylated forms are very abundantly found in nature, although the un-glycosylated form (aglycon) can occur as well.

Different plants have different profiles of flavonol glycosides. For example, onions are rich in quercetin-3,4'-diglucoside and quercetin-4'-glucoside. In addition, they contain smaller amounts of 3-glucoside, 4',7-diglucoside and of rutin (3-rutinoside). Apples contain rutin, quercetin-3-galactoside, quercetin-3-arabinofuranoside, quercetin-3-glucoside, quercetin-3-rhamnoside, quercetin-3-xyloside, quercetin-3-arabinoside. Tea contains rutin as the main flavonol, but also contains quercetin-3-glucoside, quercetin-3-galactoside, quercetin-3-rhamnoside-diglucoside. Buckwheat contains high levels of rutin in the leaves and flowers and is the main commercial source for rutin supplements on the market. Tomato contains rutin as the main flavonol. Broccoli and kale are good sources of quercetin-glycosides and contain even more kaempferol-glycosides (about twice the amount of quercetin-glycosides). Kaempferol-glycosides are routinely found in many plants alongside quercetin-glycosides but often, although not always, in much smaller quantities.

Onions, mainly yellow and red onions, are the food crops with the highest natural levels of quercetin-glycosides and typically contain about 300-600 mg/kg fresh weight (FW) of flavonols. Similar, albeit slightly lower levels are present in berries such as cranberries, lingonberries, bilberries and blackcurrants. Other major sources are apples which can have up to 100 mg/kg FW and tea which can have about 25 mg per cup of tea. Tomatoes when unmodified typically contain about 10 to 20 mg flavonols per kg FW, prototype high flavonol tomato varieties have been shown to contain 350 mg/kg FW, whilst concentrated tomato paste made from such prototypes contains about 1200 mg/kg FW.

In unmodified tomato fruits, the main flavonoid found is naringenin chalcone (Hunt et al, Phytochemistry, 19, (1980), 1415-1419). It is known to accumulate almost exclusively in the peel and is simultaneously formed with colouring of the fruit. In addition to naringenin chalcone, glycosides of quercetin and, to a lesser extent, kaempferol are also found in tomato peel.

Verhoeyen M. et al "Increasing antioxidant levels in tomatoes through modification of the flavonoid biosynthetic pathway" J Exp Botany (2002) 377: 2099-2106, outlines the various approaches to enhance flavonoid biosynthesis in tomatoes. Methods for increasing the production of flavonoids in plants by manipulating gene activity in the flavonoid biosynthetic pathway are disclosed in WO-A-99/37794, WO-A-00/04175 and EP 1254960.

An elevated blood pressure or hypertension has a prevalence of about 15% in Western populations and is increasing in developing countries. Above the age of 65 the incidence increases to approximately 35%. Hypertension is an established and independent risk factor for coronary heart disease (CHD), kidney and heart failure and stroke and may lead to disability and premature death. Lowering blood pressure in hypertensive subjects is effective in reducing the risk and disability of associated diseases. Specifically, published epidemiological studies have shown that lowering blood pressure in humans by even a few mmHg reduces the incidence of several cardiovascular diseases. For example, lowering systolic blood pressure by 5 mmHg reduces all-cause mortality by 7% on a population basis, while coronary heart disease and stroke was reduced by 9 and 14%, respectively (Whelton et al. (2002) JAMA 288:1882-1888).

Spontaneously Hypertensive Rats (SHR) are considered to be a representative model of human essential hypertension. These rats are generally used to understand the development and establishment of hypertension and to determine the blood pressure lowering effect of newly synthesised anti-hypertensive drugs. In a recent study by Duarte et al., "Effects of chronic quercetin treatment on hepatic oxidative status of spontaneously hypertensive rats" Mol. Cell Biochem (2001) 221:155-160, it was shown that SHR are characterised by increased hepatic and plasma malondialdehyde concentrations, indicating increased oxidative stress. Duarte's group further found that treatment of SHR with quercetin aglycone reduced blood pressure, increased glutathione peroxidase activity and reduced both plasma and hepatic malondialdehyde levels. It was concluded that quercetin aglycone therefore shows both antihypertensive and antioxidant properties in this model of genetic hypertension (SHR).

SUMMARY OF THE INVENTION

We have now found that plant or plant extracts, preferably tomatoes or tomato extracts, which are enriched in glucosylated flavonols can demonstrably lower blood pressure in a mammal such as SHR. Although flavonols are mainly found in nature in the glycosylated form, the proportion containing glucose residues (glucosylated) is relatively low. The finding that foods enriched in glucosylated flavonols, naturally occurring substances which can be incorporated as part of a regular diet, can lower blood pressure is significant.

Accordingly, a first aspect of the present invention provides the use of a plant which has been modified to produce increased levels of flavonol glucosides, or an extract thereof containing flavonol glucosides in the manufacture of a composition, such as a foodstuff, dietary supplement or medicament for use in reducing hypertension.

In a related aspect, the present invention provides a method of treating hypertension in a mammal which method comprises administering to the mammal a plant which has been modified to produce increased levels of flavonol glucosides, or an extract thereof containing flavonol glucosides.

According to a second aspect there is provided a food product or health supplement comprising a plant which has been modified to produce increased levels of flavonol glucosides, or an extract thereof containing flavonol glucosides.

Preferably the plant is a fruit or a vegetable.

Preferably, the plant has been genetically modified to produce increased levels of flavonol glucosides.

Preferably the flavonol glucoside is a flavonol-3-glucoside, such as isoquercitrin (quercetin-3-glucoside)

Preferably the flavonol glucoside is a quercetin glucoside.

Alternatively, the flavonol glucoside can be purified from a plant material or produced synthetically. Accordingly, the present invention provides a method of treating hypertension in a mammal which method comprises administering to the mammal, such as a human, a flavonol glucoside, as well as the use of a flavonol glucoside in the manufacture of a composition, such as a foodstuff, dietary supplement or medicament, for use in treating hypertension. Preferably the flavonol glucoside is a flavonol-3-glucoside, such as isoquercitrin (quercetin-3-glucoside)

Preferably the flavonol glucoside is a quercetin glucoside.

Preferably the flavonol glucoside is a naturally occurring flavonol glucoside

In a preferred embodiment, the flavonol glucoside is in a substantially isolated and purified form, i.e. substantially free of other plant materials, typically combined with a pharmaceutically acceptable carrier or diluent. Preferably the flavonol glucoside is at least 90 or 95% pure.

DETAILED DESCRIPTION OF THE INVENTION

Flavonol glucosides for use according to the present invention are typically obtained from plant sources. However, the normal levels of flavonol glucosides in many plants are fairly low. Thus, when the plant per se is used it will generally have been modified to exhibit increased levels of flavonol glucosides, typically as compared with the corresponding wild type plant. Accordingly, it is desirable to modify plants so as to increase the levels of flavonol glucosides produced by the plant. This can be achieved by conventional cross-breeding or by genetic manipulation as described below.

Where a plant extract is used, the level of flavonols exhibited in the plant is not as important as the extract may be manufactured to contain any desired concentration of flavonols. Plant extracts include processed forms of the plant that have essentially been subject solely to mechanical processing, such as pastes and purees, as well as solvent extracted materials. Where extracts are produced by solvent extraction, solvents should be selected that are capable of extracting flavonols. Preferred solvents are those that are compatible with food use and/or pharmaceutical use.

Preferably, the plants according to the invention are plants with a history of human consumption. Suitable plants are for example vegetables, fruits, nuts, herbs, spices, infusion materials. Suitable vegetables are for example from the Pisum family such as peas, family of Brassicae, such as green cabbage, Brussel sprouts, cauliflower, the family of Phaseolus such as barlotti beans, green beans, kidney beans, the family of Spinacea such as spinach, the family of Solanaceae such as potato and tomato, the family of Daucus, such as carrots, family of Capsicum such as green and red pepper, and berries for example from the family of Ribesiaceae, Pomaceae, Rosaceae, for example strawberries, black berries, raspberries, black currant, bilberry, lingonberry, cranberry and edible grasses from the family of Gramineae such as maize, and citrus fruit for example from the family of Rutaceae such as lemon, orange, tangerine. Also preferred are plants which can form the basis of an infusion such as black tea leaves, green tea leaves, jasmin tea leaves. Also preferred is buckwheat.

A particularly preferred plant for use in the method according to the invention is the tomato plant.

Some plants however have naturally high levels of flavonol glucosides and such plants may be used without the need to subject the plant to modifications. "Naturally high" in this context means about 15 mg flavonol glucosides/kg FW and above.

An "increased" level of flavonoids is used throughout this specification to express that the level of specific flavonoids in a transformed plant differs from the level of flavonoids present in untransformed plants. Preferably, the level of flavonoids is at least 2 or 4 times higher than in similar untransformed plants, more preferably from 10 to 100 times higher than in similar untransformed plants. Where the modified plant is one that has been obtained by conventional cross-breeding, the comparison is between parental strains and resulting hybrids, such as the F1 hybrid.

Preferably, the fruit or vegetable has been genetically modified to exhibit increased levels of flavonol glucosides compared to the wild type plant. By genetically modified it is meant that the plant comprises heterologous polynucleotide sequences, typically DNA sequences, that direct expression in the plant of gene products, typically proteins, that modulate production of flavonol glucosides. 'Heterologous' is understood by persons skilled in the art to mean polynucleotide sequences that have been artificially introduced and are foreign to the plant. This definition includes additional copies of coding sequences that are already found in the plant's genome. Heterologous sequences will typically be integrated into the host cell chromosomes, preferably stably integrated.

Modulation of flavonol glucoside production can be achieved by several means e.g. introduction of coding sequences for enzymes in the biosynthetic pathway and/or introduction of sequences encoding transcriptional/translational regulators of the expression of enzymes in the biosynthetic pathway. Other approaches include modifying the regulatory sequences e.g. promoter/enhancer regions, of endogenous genes.

Methods for manipulating the production of flavonoids in plants by manipulating gene activity in the flavonoid biosynthetic pathway are disclosed in WO99/37794, WO00/04175, EP 1254960 and Verhoeyen M. et al "Increasing antioxidant levels in tomatoes through modification of the flavonoid biosynthetic pathway" J Exp Botany (2002) 377: 2099-2106. For example, WO00/01475 describes transformed tomato plants that have significantly increased levels of the flavonol glucoside isoquercitrin, this flavonol glucoside not being present in the unmodified plants. These plants also have increased levels of rutin. However, the bioavailability of rutin is much lower than the glucoside isoquercitrin and therefore it is the increase in isoquercitrin which is relevant to the present invention.

It will of course be understood that the plant does not have to be genetically modified to provide "increased" levels of flavonoids. Such plants can be developed by conventional cross-breeding.

Measuring the amount of flavonol glucosides in fruit or vegetables can be carried out using known techniques such as HPLC as shown in WO-A-99/37794 and WO 00/04175. Thus, the skilled man would be able to determine the level of flavonol glucosides in a plant and compare that to the levels normally produced in the wild type plant to determine whether flavonol glucoside production was "increased" or "naturally high", using the techniques outlined in WO-A-99/37794 and WO 00/04175.

Where a plant extract is used, the "increase" or "alteration" in the levels of flavonols of the plant being used may be minimal over the wild type plant, or the wild type plant itself may be used. When a plant extract is used, the concentration of the flavonol may be determined without reference to the plant the extract is derived from. Hence, the plant extract concentration is determined independently to that of the plant it is derived from. The plant extract may be from a modified or unmodified plant. The important feature is that the plant extract provides the required minimum dosage of flavonol glucosides.

Modification of a plant to up-regulate flavonoid synthesis can occur using several different techniques, as follows.

For example, through the ectopic expression of either a select number of key biosynthetic genes or key regulatory elements, or a combination of both. In peel tissue, chalcone isomerase (CHI) gene activity appears to be critical in WO 00/04175 and expression of a sequence encoding the P. hybrida chalcone isomerase has been shown to lead to a large increase in the level of quercetin-glycoside accumulation. It has further been demonstrated in EP 1254960 that concomitant expression of the sequences encoding chalcone synthase (CHS) and flavonol synthase (FLS) from P. hybrida is sufficient to achieve accumulation of kaempferol-glycosides in tomato flesh. In addition, studies have shown that ectopic expression of three genes encoding the biosynthetic enzymes CHS, CHI and FLS achieve increased flavonol accumulation throughout tomato fruit. Alternatively, ectopic expression of the regulatory genes Lc and C1, together with the biosynthetic gene CHI results in a similar phenotype.

Most preferably, the fruit is a genetically modified tomato which exhibits increased levels of flavonol glycosides, such as the tomatoes described in WO 00/04175. Specifically, tomato plants can be transformed with a sequence from P. hybrida encoding CHI, under the control of the strong constitutive double CaMV35S promoter. Analysis of such transformants containing the CHI transgene show a dramatic increase in fruit peel flavonol levels compared with control plants, up to 78-fold increase in individual fruits. This rise in total flavonol accumulation mainly comprised increases in the accumulation of rutin (quercetin 3-O-rutinoside), isoquercitrin (quercetin-3-O-glucoside) and kaempferol-3-O-rutinoside in the peel tissues.

An alternative method according to WO-A-99/37794 and Bovy et al, "High-flavonol tomatoes resulting from the heterologous expression of the maize transcription factor genes Lc and C1" The Plant Cell (2001), 14, 2509-2526, which may be used involves transforming the tomato with transcription factors such as Lc and C1. In general, this method may involve the incorporation of two or more polynucleotide sequence/genes each encoding a different transcription factor for flavonoid biosynthesis, or a sequence functionally equivalent thereto, each being operably linked to a promoter.

In a further alternative approach, P. hybrida sequences encoding each of the key biosynthetic enzymes leading to flavonols, chalcone synthase (CHS), chalcone isomerase (CHI), flavonone-3-hydroxylase (F3H), and flavonol synthase (FLS) were ectopically expressed simultaneously. HPLC analyses of primary transformants containing all four transgenes showed that these tomato lines accumulate very high levels of quercetin glycosides in the peel and, more modest, but significantly increased levels of kaempferol- and naringenin-glycosides in columella tissue (Colliver et al., Phytochemistry Reviews (2002) 1:113-123. Improving the nutritional content of tomatoes through reprogramming their flavonoid biosynthetic pathway). The high quercetin phenotype in the peel was expected because of the presence of the CHI transgene, and it is noteworthy that the levels detected were similar to those found in CHI-only transformants.

In addition to the 'single gene' transformants, 'two-gene' combinations can be used which involve crossing of parent plants harbouring single gene constructs. HPLC analyses of fruit from these transformed lines revealed that the genes that appear to be critical in leading to flavonol biosynthesis in tomato flesh (pericarp and columella) tissue are CHS and FLS. As described by Colliver et al, ectopic expression of CHS resulted in modified tomatoes accumulating increased levels of naringenin-glycosides but with no increase in flavonols. By contrast, analysis of tomatoes harbouring the FLS transgene showed that no significant difference in biochemical phenotype was detectable when compared to control fruit. The analyses have shown that concomitant expression of both CHS and FLS has a synergistic effect resulting in a significant accumulation of both naringenin- and kaempferol-glycosides in tomato flesh.

The plant, preferably fruit or vegetable, exhibiting increased levels of flavonol glucosides may be administered in different forms such as in food products or health supplements. It is to be understood that the plant per se may be used or a plant extract with high or "naturally high" levels of flavonols may alternatively or additionally be used.

For example, once harvested the plants may be eaten as such. Alternatively, the fruit or vegetables may be used in the production of food products or health supplements. For example parts of the fruit or vegetable may be added to salads. Also, heat-treatment may be applied, for example tomatoes may be used to prepare tomato sauces with tomato as one of the main ingredients (e.g. at levels of about 10% by weight or more, for example 80% by weight or more) such as tomato paste, tomato ketchup, pizza sauce, pasta sauce, dressings etc. Also the tomatoes may be used to prepare products like tomato juice, tomato soups etc.

In addition, the food products can be selected from the group consisting of nutritional supplements, spreads, margarines, creams, sauces, dressings, mayonnaises, ice creams, fillings, confectioneries, health bars, cereals, health drinks. In this case an extract of the fruit or vegetables or other plants such as tea, onions or buckwheat exhibiting high levels of flavonoids may be used.

In addition to the above components the blends and the food products can contain other micronutrients, examples thereof being anti oxidants (Vitamin C or Vitamin E), other vitamins in particular Vitamin B1, B6 and B12, Vitamin K, folic acid, minerals like calcium, magnesium, iron, copper, or zinc, however, emulsifiers also can be present as well as minor amounts of polyunsaturated fatty acids in particular DHA.

Preferably, the food product or health supplement contains sufficient levels of flavonol glucosides to allow a daily intake equivalent to at least 0.1 mg quercetin aglycon per kg of bodyweight, more preferably at least 1, 5, 10 or 20 mg per kg of bodyweight. For example, a food product which is served in portion sizes of 100 g or more should preferably contain at least 10 mg per 100 g, more preferably at least 20, 50, or 100 mg per 100 g. A food product, such as a snack, with a weight of less than 100 g, or a dietary supplement, should preferably contain at least 10 mg of flavonol glucosides, more preferably at least 20, 50 or 100 mg.

Any plant, preferably a fruit or vegetable which exhibits naturally high increased, or increased levels of flavonol glucosides, preferably quercetin glucosides, can be used to reduce hypertension in mammals. Most preferably isoquercitrin is used, optionally in combination with rutin.

Preferably, the daily dose of flavonols provided by the plant or plant extract is the amount of flavonol glucosides equivalent to from about 0.1 to 20 mg of quercetin aglycon per kg of body weight (BW), more preferably from about 1 to 20 mg of quercetin aglycon per kg of BW, even more preferably from 10 to 20 mg of quercetin aglycon per kg of BW.

For example, for 10 mg quercetin aglycon equivalent, you need about 20 mg rutin or 14 mg isoquercitrin (the molecular weight (MW) of quercetin is 338.26, and the MW of isoquercitrin and rutin are 464.4 and 610.53 respectively).

The application will now be described with reference to the following non-limiting examples.

DETAILED DESCRIPTION OF THE DRAWINGS

FIGS. 1a and b show the change in average diastolic blood pressure of SHR relative to the average diastolic blood pressure in week 0, during the period from 9 am to 7 am.

1a. Change in average diastolic blood pressure relative to average diastolic blood pressure in week 0 is shown for each diet group for week 0 and for the 5 weeks of experimental food.

1b. Change in average diastolic blood pressure relative to average diastolic blood pressure in week 0 is shown for each diet group for week 5 of experimental food.

Figure 2:
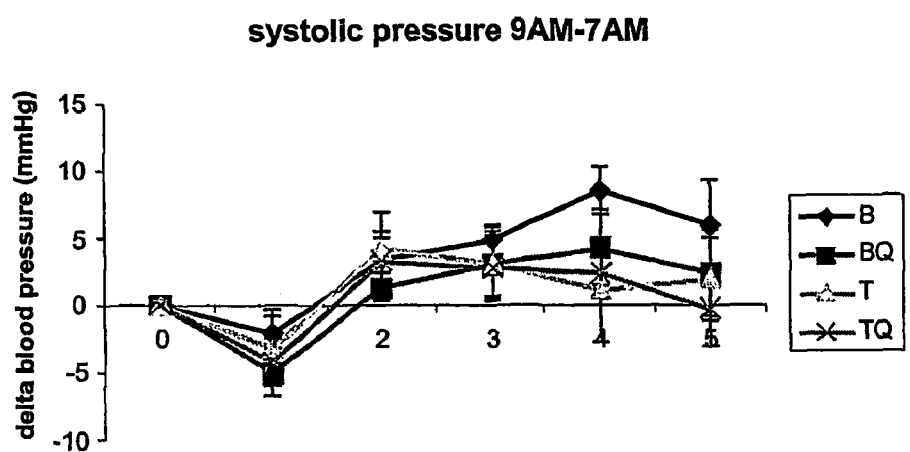
Figure 2:
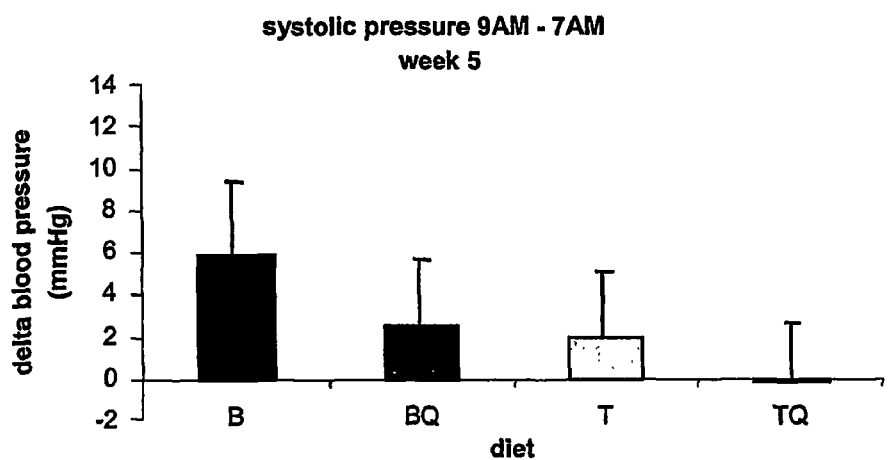

FIGS. 2a and b show the change in average systolic blood pressure of SHR relative to average systolic blood pressure in week 0, during the period from 9 am to 7 am 2a. Change in average systolic blood pressure relative to average systolic blood pressure in week 0 is shown for each diet group for week 0 and for the 5 weeks of experimental food.

2b. Change in average systolic blood pressure relative to average systolic blood pressure in week 0 is shown for each diet group for week 5 of experimental food.

Figure 3:
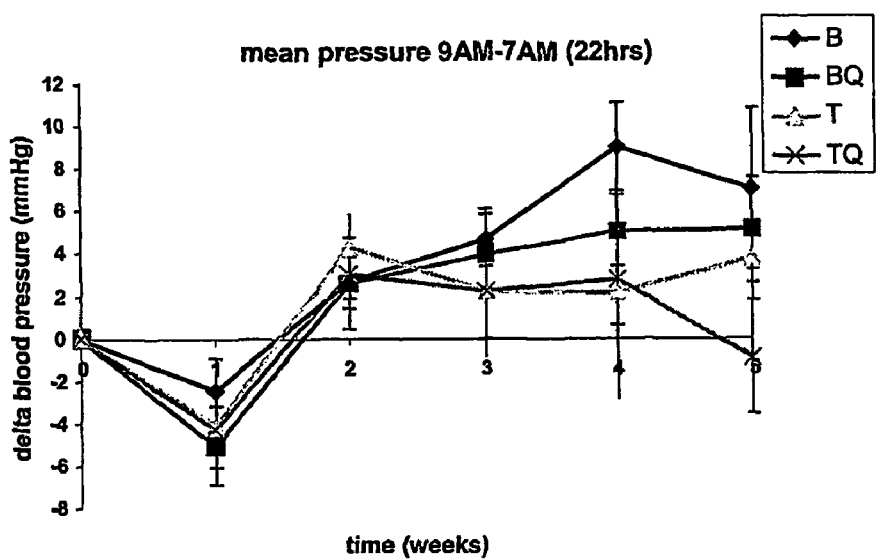
Figure 3:
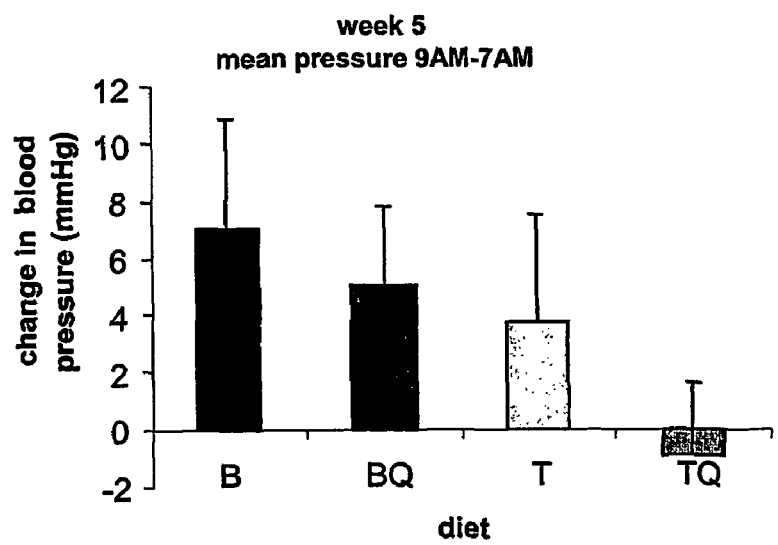

FIGS. 3a and b shows the change in average mean blood pressure of SHR relative to average mean blood pressure in week 0, during the period from 9 am to 7 am.

3a. Change in average blood pressure relative to average mean blood pressure in week 0 is shown for each diet group for week 0 and for the 5 weeks of experimental food.

3b. Change in average mean blood pressure relative to average mean blood pressure in week 0 is shown for each diet group for week 5 of experimental food.

Figure 4:
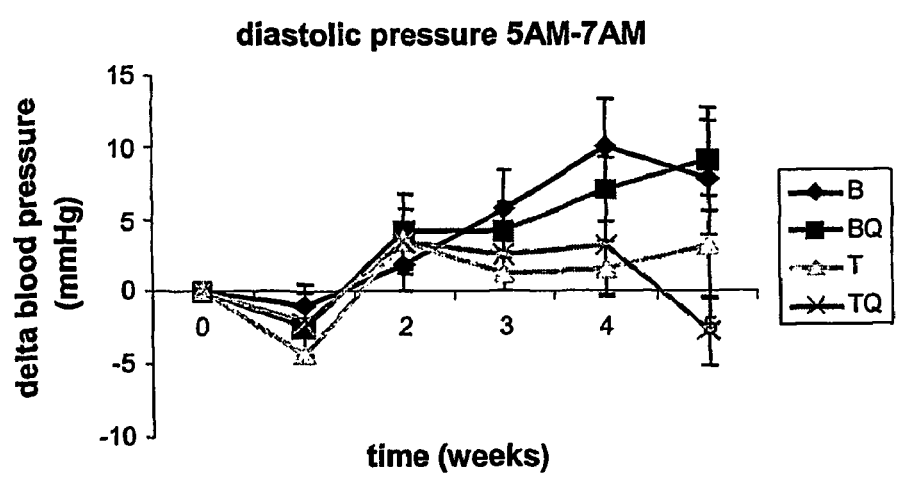
Figure 4:
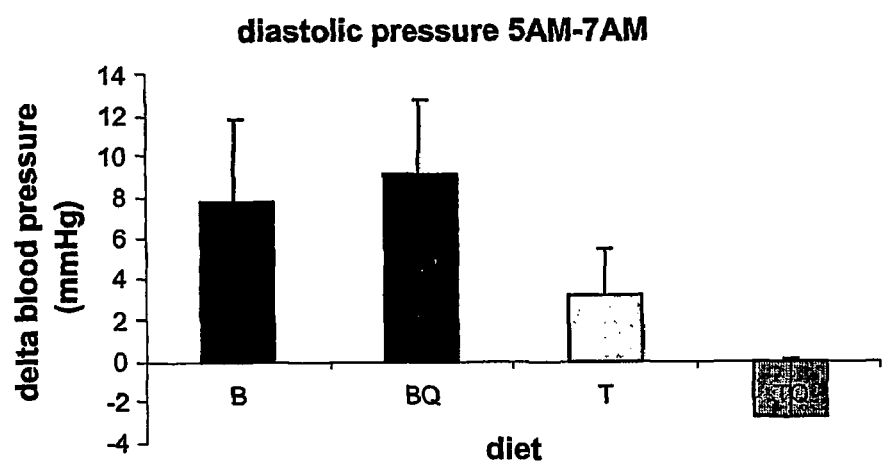

FIGS. 4a and b show the change in average diastolic pressure in SHR relative to average diastolic blood pressure in week 0, during the period from 5 am to 7 am (early morning period).

4a. Change in average diastolic blood pressure relative to average diastolic blood pressure in week 0 is shown for each diet group for week 0 and for the 5 weeks of experimental food.

4b. Change in average diastolic blood pressure relative to average diastolic blood pressure in week 0 is shown for each diet group for week 5 of experimental food.

Figure 5:
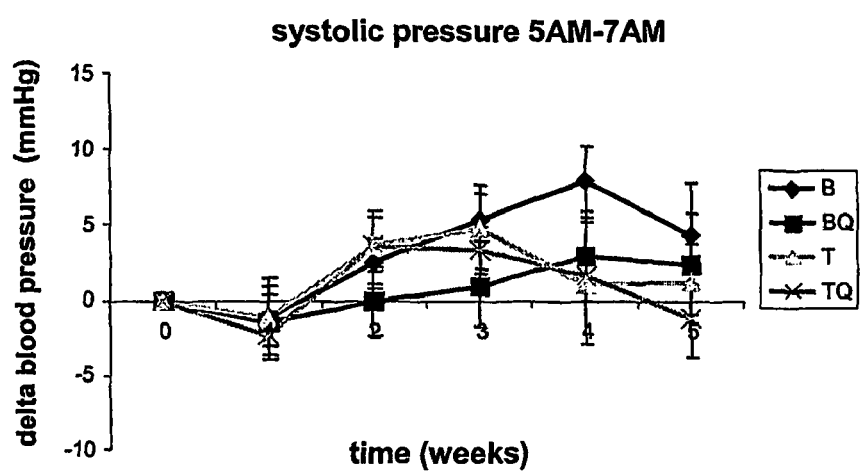
Figure 5:
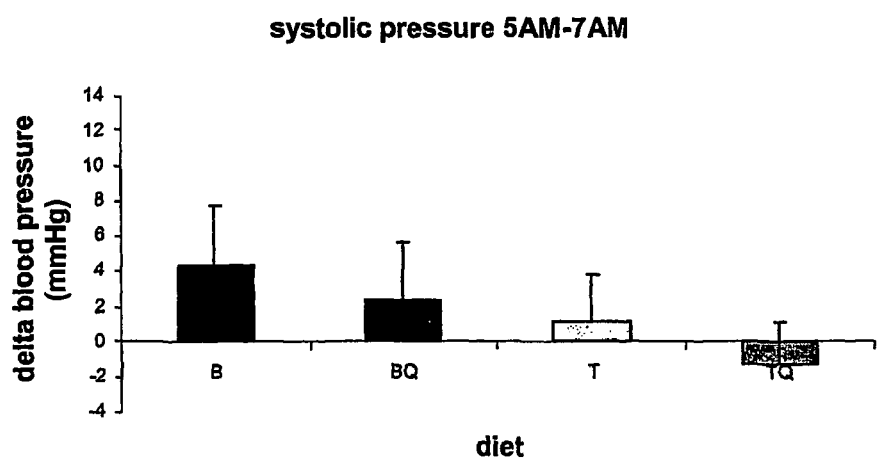

FIGS. 5a and b show the change in average systolic pressure in SHR relative to average systolic blood pressure in week 0, during the period from 5 am to 7 am (early morning period).

5a. Change in average systolic blood pressure relative to average systolic blood pressure in week 0 is shown for each diet group for week 0 and for the 5 weeks of experimental food.

5b. Change in average systolic blood pressure relative to average systolic blood pressure in week 0 is shown for each diet group for week 5 of experimental food.

Figure 6:
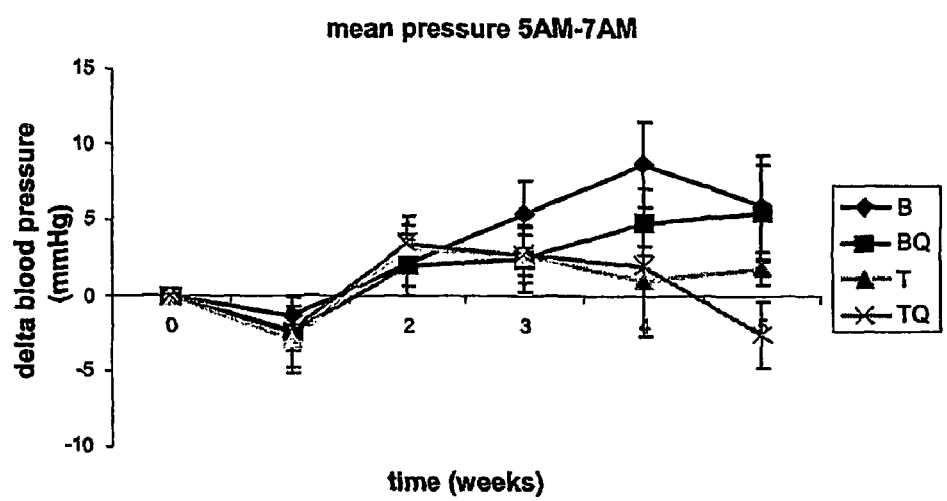
Figure 6:
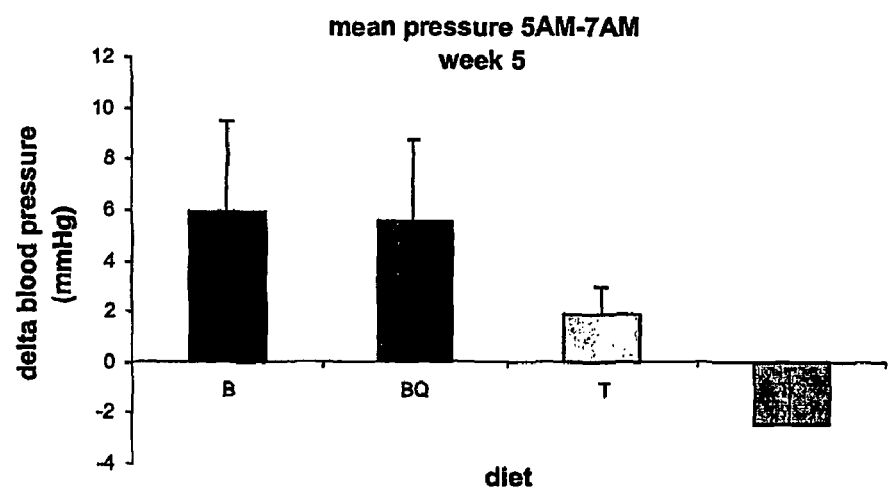

FIGS. 6a and b show the change in average mean pressure in SHR relative to average mean blood pressure in week 0, during the period from 5 am to 7 am (early morning period).

6a. Change in average mean blood pressure relative to average mean blood pressure in week 0 is shown for each diet group for week 0 and for the 5 weeks of experimental food.

6b. Change in average mean blood pressure relative to average mean blood pressure in week 0 is shown for each diet group for week 5 of experimental food.

EXAMPLES

Overview of Protocol

The effects of a tomato paste, enriched with quercetin-glycosides (mainly rutin and isoquercitrin), on blood pressure were examined on Spontaneously Hypertensive Rats (SHR). SHR are extensively used in research to assess the effects of bioactive agents on blood pressure.

The SHR were equipped with a blood pressure measuring telemetry device that allows blood pressure to be continuously and non-invasively monitored. Flavonol enriched tomato paste in different forms was administered via the diet of the rats. The effects of this diet (flavonol enriched tomato paste) was compared with a control tomato paste (contains a low level of flavonols), a diet containing pure quercetin aglycon and a flavonoid-free diet.

Blood pressure was measured for a period of 10 seconds every 5 min over 24 hours for 3 consecutive days per week using a telemetry device. Each diet was administered for a period of 5 weeks.

Screening of Tomato Pastes to Determine Flavonol Levels

A rapid screening method was required for the differentiation of high and low flavonoid tomato pastes to be used in the rat clinical trial. Rutin (quercetin-3-rutinoside) and Isoquercitrin (quercetin-3-glucoside) are the primary flavonoids (flavonol glycosides) of interest (in the high flavanoid pastes, rutin is about 60%, isoquercitrin is about 25-33% and other glycosides+quercetin aglycon constitute about 7-15% of the total flavanoid content). Both thin layer chromatography procedures and UV spectrophotometric procedures can be used as quality control procedures. Flavonoids (both aglycone and flavonol glycosides) typically show characteristic absorbancies at 270 nm and 370 nm.

Sample Extraction

A sample of low flavonoid paste and a sample of high flavonoid paste 1 g+/−0.1 g of paste was put into a 15 mL screw capped glass vial. 10 mL of methanol was added and the mixture was vibromixed thoroughly for 1 minute. The tube was heat sealed on a Pierce Reacti-Therm (or equivalent) heated block for 30 minutes at 60° C., vibromixing the mixture every 5-10 minutes, preferably within a fume cupboard. The mixture was allowed to cool. If required the sample tubes were centrifuged on a bench top centrifuge (swing-out) for 10 minutes at 2000 rpm. The clear upper methanol layer was pipetted off into a clean glass vial. The methanol was filtered through a 0.2 μM PTFE syringe filter to remove both lycopene and any residual solid material.

Screening by UV Spectrophotometry

Methanol extracts characterised under UV light can be more quantitatively characterised by UV Spectrophotometry. The solutions were diluted typically by a factor of 10:1 and their UV absorbance spectra determined 190 nm-600 nm.

Using cuvettes suitable for UV measurements down to 190 nm, methanol was placed in both the reference and sample positions in the UV spectrometer. The "blank" solvent background spectrum was checked and established. Cuvettes used for sample analysis required thorough rinsing with methanol and drying with tissue and under nitrogen between measurements. The spectra ranging 190 nm-600 nm of an approximately 0.01 mg/mL solution of rutin standard (Sigma) in methanol was measured. The spectral maxima typically observed 260 nm-270 nm and 360 nm-370 nm was recorded. The spectrum and absorbance maxima obtained for rutin are shown in Table 1. The control paste and high flavonoid paste were analysed as methanol extract solutions by determining the spectra ranging 190 nm. The absorbance was recorded at the observed spectral maxima for each sample typically 260 nm-270 nm and 360 nm-370 nm as shown in Table 2.

TABLE 1

Absorbance Maxima Measured For Rutin Standard (0.1 mg/mL)

| Sample | Absorbance Wavelength | |
|---|---|---|
| | 359.0 nm | 258.5 nm |
| Rutin standard | 0.28 | 0.32 |

TABLE 2

Absorbancies For Control And C11+ High Flavonoid Tomato Pastes (Literature Maxima of 270 nm and 370 nm)

| Sample | Absorbance Wavelength | |
|---|---|---|
| | 370.0 nm | 270.0 nm |
| Control Paste | 0.1406 | 1.1006 |
| C11 + High Flavonoid | 0.4368 | 1.3793 |

Protocol for SHR Testing

Design of the Study

24 SHR were used in the study and they were equipped with a blood pressure measuring telemetry device to be continuously and non-invasively monitored. Four diets were given in an incomplete block design of 2×5 weeks intervention. All rats had an acclimatisation period (week 0), feeding training and reversal of circadian rhythm (week 1), implantation of transmitter and a recovery period (weeks 2 and 3) and a run-in period (week 4) prior to the interventions Test System Using Male, Spontaneously Hypertensive Rats (SHR)

The age of the rats at the beginning of the first intervention ranged from 11 to 16 weeks. The animals were marked with their animal number by means of an earmark. Throughout the study the animals were housed individually in reversed 12 hrs light/12 hours dark-cycle 9 from 8.00-till 8.00 with free access to drinking water.

Test Article

The test substance in this study was given via the diet. The diets were given according to an incomplete block design, which means that every rat received 2 of the 4 diets. Water was supplied ad libitum 24-hours a day. The experimental diets (diet B, BQ, T and TQ) were given between 8.00-9.00 AM ( just before start of the dark period). The amount of experimental diet was adjusted to the mean weight of the rats which receive the experimental diet, approximately 2.5 g porridge or paste/100 g body weight. After the experimental diet all rats received ad libitum the flavonoid-free semi-synthetic diet (diet B) from 9.00 AM-4.00 PM. If some of the experimental diet was left it was mixed thoroughly with the upper part of the flavonoid-free semi-synthetic diet. From 4.00 PM until 8.00 AM the following day the rats received no food.

The following test diets were used in the study:

Diet B—flavonoid-free semi-synthetic diet.

The composition of this diet is given in Table 3. Portions of the semi-synthetic diets were prepared prior to each 4 or 5-week feeding period and stored at −20° C. in aliquots suitable for one day of feeding. These aliquots were thawed and mixed appropriately with water prior to use.

TABLE 3

Flavonoid-free semi-synthetic diet:

| Total diet composition: Diet B | | | |
|---|---|---|---|
| Ingredient | grams per/kg | en % | kJ |
| Calcium-caseinate (15.7 kJ/g) | 150.5 | 16 | 2357.7 |
| Vitamin-mixture | 10.7 | | |
| Mineral-mixture | 36.7 | | |

TABLE 3-continued

| | | | |
|---|---|---|---|
| Arbocel BC-200 | 52.5 | | |
| Fat blend (37.7 kJ/g)* | 78.3 | 20 | 2947.1 |
| Choline Bitartrate | 2.6 | | |
| L-cysteine Hydrochloride | 1.9 | | |
| Maize starch (13.7 kJ/g) | 667.0 | 64 | 9430.6 |
| Total | 1000 | 100 | 14735.4/kJ |

*Composition of the fat blend: SAFA:MUFA:PUFA = 1:1:1
Coconut oil   5.00 grams
Hozol         2.46 grams
Lard         49.02 grams
Palm oil      1.00 gram
Sunflower    42.53 grams Vitamin mix

| Ingredient | g/kg mix |
|---|---|
| Nicotinamide | 3.00 |
| $Ca^{++}$pantothenate | 1.60 |
| Pyridoxine B6 | 0.70 |
| Thiamine monitr. B2 | 0.60 |
| Riboflavine B1 | 0.60 |
| Folic acid | 0.20 |
| Biotin | 0.02 |
| Vitamin B12 | 5.00 |
| Vitamin E (50%) | 15.00 |
| Vitamin A, 500000 IE | 0.80 |
| Vitamin $D_3$ | 1.00 |
| Vitamin $K_1$ (phylloq) | 0.10 |
| Maize starch | 971.38 |
| Total | 1000.00 |

Mineral mix

| Ingredient | | g/kg mix |
|---|---|---|
| Calcium Carbonate | $CaCO_3$ | 236.91 |
| Potassium-dihydro phospate | $KH_2PO_4$ | 196.00 |
| Sodium chloride | NaCl | 74.00 |
| Magnesium oxide | MgO | 24.00 |
| Potassium citrate | $C_6H_5K_3O_7 \cdot H_2O$ | 70.78 |
| Potassium sulphate | $K_2SO_4$. | 46.60 |
| AIN mineral mix* | | 91.71 |
| Maize starch | | 260.00 |
| Total | | 1000.0 |

AIN mineral mix*

| Ingredient | | g/100 g mix |
|---|---|---|
| Potassium chromium(III)sulphate | $CrK(SO4) \cdot 12H2O$ | 0.2750 |
| Cupper carbonate | $CuCO3 \cdot Cu(OH)2$ | 0.3000 |
| Sodium fluoride | NaF | 0.0635 |
| Potassium iodate | KIO3 | 0.0100 |
| Iron-citrate | $C6H5FeO7 \cdot 5H2O$ | 6.0600 |
| Manganese carbonate | MnO3 | 0.6300 |
| Sodium selenite | Na2SeO3 | 0.0154 |
| Zinc carbonate | $ZnCO3 \cdot 2Zn(OH)2 \cdot H2O$ | 1.6500 |
| Sodium molybdate | $Na2MoO4 \cdot 2H2O$ | 0.0110 |
| Sodium meta-silicate | Na2SiO3 | 1.4500 |
| Litium Chloride | LiCl | 0.0174 |
| Boronic acid | H3BO3 | 0.0815 |
| Nickel carbonate | $2NiCO3 \cdot 3Ni(OH)2 \cdot 4H2O$ | 0.0318 |
| Ammoniumvanadate | NH4VO | 0.0066 |
| Maize starch | | 81.1080 |
| Total | | 91.71 |

For the experimental diet 1 g powder was mixed with 1.5 ml water per 100 g body weight of the rat. For the diet between 9.00 AM-4.00 PM the powder was mixed 1:1, approximately 40 g porridge per rat was given. The porridge was freshly made every morning.

Diet BQ—Semi-synthetic Diet Containing Pure Quercetin Aglycone

This diet consists of the flavonoid-free semi-synthetic diet containing 3 g quercetin/kg powder diet B. The powder was used directly after thawing and was mixed with water, i.e. 1 g powder+1.5 ml water per 100 g body weight of the rat. The diet was freshly made every morning.

Diet T—Normal Tomato Paste (Not Enriched)

Normal tomato paste was used which contained an equivalent of 1.73 mg quercetin aglycone/100 g wet weight paste (as determined by HPLC analysis). Immediately before the paste was used the flavonol level was qualitatively checked by UV spectroscopy. The amount of tomato paste given to the rat every day was 2.5 g/100 g BW. This paste does not contain any isoquercitrin (quercitin-3-glucoside).

Diet TQ—Tomato Paste from Genetically Modified Tomatoes

The tomato paste from genetically modified tomatoes made in accordance with WO 00/04175 which contained the equivalent of 48.8 mg quercetin aglycone per 100 g wet weight paste was used (level determined by HPLC analysis). A qualitative check was carried out immediately before use as described above (T-diet). As expected all tomato paste from genetically modified tomato samples contained high flavonoid levels. The amount of tomato paste given to the rat every day was 2.5 g/100 g BW. This tomato paste contains enhanced levels of isoquercitrin and rutin.

Determination of Blood Pressure (Telemetry)

Blood pressure was measured every 5 minutes for 10 seconds for 3 consecutive days per week and per rat. The different parameters, i.e. systolic, mean, diastolic pressure, were calculated. The mean of a specific parameter for a specific period of a day per rat was calculated. The value per week was calculated as the mean value of the 3 separate days. The results per rat are expressed as an increase or decrease of the specific parameter compared to week 0 (mmHg).

The specific time periods were:
9 AM-7 AM (22 hrs)
5 AM-7 AM (early morning period)

In the analysis, the results of the $1^{st}$ and $2^{nd}$ intervention periods were combined.

The week numbers used in the analysis is as follows:
wk 0=week before intervention (run-in+last week of wash-out)
wk 1-5=$1^{st}$-$5^{th}$ intervention weeks In this way 41 rats were analysed. This should have been 48 but because of transmitter-tip 'silting' a loss of a number of signals occurred.

Paste Samples

Immediately after opening each can of paste (GM and control), a 5-10 g sample of the paste was taken and stored at −20° C. for future flavonol analysis by HPLC. In addition, a small sample of the paste was used on the day of diet preparation and prior to administration, for crude analysis by UV spectrometry to confirm whether the paste had low or high levels of flavonols.

Results

The results shown in FIGS. 1 to 6 clearly demonstrate a link between the reduction of hypertension and the administration of tomato paste which exhibits high flavonol glycoside/glucoside levels.

Systolic blood pressure and diastolic blood pressure are indicators or risk factors of cardiovascular events in later life (Safar M. E. "Epidemiological Findings Imply That Goals for Drug Treatment of Hypertension Need to be Revised" (2001) Circulation 103:1188-1190). Systolic blood pressure is believed to be a good measure of hypertension.

There is a consistent trend for a time dependent increase in blood pressure of the SHRs. As shown in the figures, the only diet that seems to be able to counteract this increase is the diet containing high levels of flavonol glycosides, including the glucoside isoquercitrin (TQ). This is most notable for the diastolic blood pressure during the early morning period, where after 5 weeks the group fed a basic diet lacking flavonols shows an increase in average diastolic blood pressure of 8 mm Hg relative to week 0, whereas the group fed the TQ diet shows an average decrease of 3 mm Hg relative to week 0. The resulting difference in average diastolic blood pressure between those two groups, after 5 weeks, is therefore approx 11 mm Hg. The differences in average mean blood pressure show the same trend. The differences in average systolic blood pressure are smaller but still follow the same trend. Given that relatively modest reduction in blood pressure can lead to substantial decreases of cardiovascular risk factors, the observed effects are significant. Moreover these results raise the possibility of providing food products with blood pressure lowering effects. Consequently, people at risk of becoming hypertensive may delay this possibility without taking medication.

It should be noted that although the modified tomato paste contains both isoquercitrin and enhanced levels of rutin and, it has been established that rutin has poor bioavailability compared with quercetin glucosides such as isoquercitrin and is therefore unlikely to play a significant role in vivo in lowering hypertension.

Interestingly, the SHRs fed ordinary tomato paste exhibited a slower rate of time dependent blood pressure increase, compared to the B and BQ fed rats. This could possibly be explained by the fact that ordinary tomato paste contains low levels of flavonol glycosides, mainly rutin, which despite being less bioavailable may still exert a low level effect.

As noted earlier, even small blood pressure decreases contribute to reductions of cardiovascular and all-cause mortality. This is true for systolic and diastolic blood pressure. In addition to the figures for systolic blood pressure, the figures for diastolic blood pressure point into the same direction. In an analysis of the Framingham Heart Study experience, Cook et al "Implications of small reductions in diastolic blood pressure for primary intervention" (1995) Arch. Int. Med. 155:701-709 reported that a 2-mm Hg reduction of diastolic blood pressure for white US residents 35 to 64 years of age would result in a 17% decrease in the prevalence of hypertension, a 14% decrease in the risk of stroke and transient ischaemic attacks, and a 6% reduction of coronary heart disease. Given the fact that the risk for cardiovascular disease is higher in people with higher blood pressure, the benefits of small blood pressure reductions among these people will be higher than the population-based numbers cited above. The present invention, therefore, shows that important risk reductions can be attained with a food containing or enriched in flavonol glucosides.

The various features and embodiments of the present invention, referred to in individual sections above apply, as appropriate, to other sections, mutatis mutandis. Consequently features specified in one section may be combined with features specified in other sections, as appropriate.

All publications mentioned in the above specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

The invention claimed is:

1. A method for the treatment of hypertension in a mammal which method comprises administering to the mammal a foodstuff, dietary supplement or medicament comprising an effective amount of a flavonol glucosides.

2. The method according to claim 1, wherein the flavanol glucoside is a quercetin glucoside.

3. The method according to claim 1, wherein the flavanol glucoside is isoquercitrin.

4. The method according to claim 1, wherein the flavanol glucoside is a naturally occurring flavanol glucoside.

5. The method according to claim 1, wherein the flavanol glucoside is in a substantially isolated and purified form.

6. The method according to claim 1, wherein the flavanol glucoside is combined with a pharmaceutically acceptable carrier or diluent.

7. The method according to claim 1, wherein the flavanol glucoside is at least 90% pure.

8. The method according to claim 1, wherein the effective amount is chosen so as to provide an equivalent of 1 to 20 mg of quercetin aglycon per kg of body weight (BW) of the mammal.

* * * * *